(12) United States Patent
Hornauer

(10) Patent No.: US 7,608,466 B2
(45) Date of Patent: Oct. 27, 2009

(54) PROCESS AND DEVICE FOR PRODUCING REAGENT CARRIERS

(75) Inventor: Hans Hornauer, Piessenberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 300 days.

(21) Appl. No.: 11/156,855

(22) Filed: Jun. 20, 2005

(65) Prior Publication Data

US 2005/0282235 A1  Dec. 22, 2005

(30) Foreign Application Priority Data

Jun. 21, 2004  (DE) ............... 10 2004 029 909

(51) Int. Cl.
*G01N 33/53* (2006.01)

(52) U.S. Cl. ............ 436/514; 435/4; 436/43; 436/44; 436/46; 436/174; 436/180; 422/56; 422/57; 422/58; 422/59; 422/60; 422/61; 422/63; 422/65; 422/66; 422/67; 422/99; 422/100

(58) Field of Classification Search ............ 422/56–61, 422/63, 65, 66, 67, 99, 100; 436/43, 44, 436/46, 174, 180
See application file for complete search history.

(56) References Cited

U.S. PATENT DOCUMENTS

| 2,932,330 | A | 4/1960 | Donofrio et al. |
| 3,260,413 | A | 7/1966 | Natelson |
| 3,526,480 | A | 9/1970 | Findl et al. |
| 4,841,786 | A | 6/1989 | Schulz |
| 5,183,508 | A | 2/1993 | Cholinski |
| 5,378,638 | A | 1/1995 | Deeg et al. |
| 5,517,702 | A | 5/1996 | Gleisner |
| 6,245,297 | B1 | 6/2001 | Kowallis |
| 6,673,533 | B1 * | 1/2004 | Wohlstadter et al. ........... 435/6 |
| 2004/0018635 | A1 | 1/2004 | Peck et al. |
| 2004/0071599 | A1 | 4/2004 | Rusch et al. |

FOREIGN PATENT DOCUMENTS

| DE | 1673340 | 2/1972 |
| DE | 60000539 T2 | 4/1999 |
| EP | 0833158 A1 | 4/1998 |
| EP | 0939319 A2 | 9/1999 |
| EP | 1380839 A1 | 1/2004 |
| GB | 1240304 | 10/1968 |
| GB | 1526708 | 9/1978 |
| WO | WO 02/00223 A1 | 1/2002 |

OTHER PUBLICATIONS

Kuhn, C. et al., "Trends in Solutions in Microarray Production," BIOforum International, Jan. 2000, pp. 30-31.

* cited by examiner

*Primary Examiner*—Bao-Thuy L Nguyen
(74) *Attorney, Agent, or Firm*—Marilyn Amick; Roche Diagnostics Operations, Inc.

(57) ABSTRACT

The invention concerns a process for producing reagent carriers having a binding capability that are suitable for determining analytes in liquids, wherein the process comprises at least one step of treating a respective reagent carrier body in particular by transferring material between a treatment device and the reagent carrier body in a preparation device and wherein this treatment step takes place on the moving reagent carrier body during its transport in the preparation device or during a movement of the treatment device relative to the reagent carrier body in the preparation device.

7 Claims, 2 Drawing Sheets

PROCESS AND DEVICE FOR PRODUCING REAGENT CARRIERS

RELATED APPLICATIONS

This application claims priority to German patent application no. 102004029909.9 filed Jun. 21, 2004.

FIELD OF THE INVENTION

The invention concerns a process for producing reagent carriers having a binding capability that are suitable for determining analytes in liquids wherein the process comprises at least one step in which a particular reagent carrier body is treated in particular by transferring material between a treatment device and the reagent carrier body in a preparation device.

BACKGROUND OF THE INVENTION

The invention concerns the economical production or preparation of reagent carriers for the qualitative or quantitative determination of analytes in liquids and in particular in body fluids. Such known reagent carriers are able to bind analyte molecules from the sample liquid on a carrier surface in a reaction ("assay") where the binding events can be detected by measurement techniques e.g. by the optical detection of fluorescence events. Reagent carriers of this type can for example be prepared with microarray structures by the process of the present invention in order to for example produce a biochip for the selective local detection of binding reactions.

However, the invention is not limited to the production of biochips with microarrays but is also suitable for producing two-dimensionally coated carriers such as microtitre plates or microtitre strips.

In the production of reagent carriers of the type considered here, an individual surface area of the previously prepared reagent carrier body is contacted with a liquid or liquids in a well defined time sequence. Preparation devices are used for this which have technical equipment for the volume-controlled addition of liquids. Furthermore, preparation devices may be used which have equipment to remove previously added liquids or to remove weakly bound or entrapped molecules or particles from the surface of the carrier body. Moreover, washing devices, drying devices etc. may also be used as treatment devices.

The preparation devices usually include a control device for controlling predetermined time sequences of process steps. The sequence of the process steps can be interrupted by waiting times that are necessary to allow the reactions to run. For this purpose the reagent carrier bodies can be transported to interim storage positions in the preparation device or outside the preparation device. The interim storage positions may be equipped with temperature control devices, shakers etc. for the reagent carrier bodies.

In conventional systems for producing or preparing reagent carriers, a particular reagent carrier body is transported to a treatment device and is subjected there in a resting state to a treatment step. After treatment the reagent carrier body is then removed from the treatment zone and optionally conveyed to another treatment device. This conventional procedure generally only allows a relatively low output of prepared reagent carriers per time unit. Proposals have already been made to run several treatment devices in parallel in one preparation device. These treatment devices are provided in a multiple design such that they can treat groups of reagent carrier bodies in parallel. Although this enables a higher throughput in the preparation of reagent carriers, the problem arises that different results occur in the treatment of the individual reagent carrier bodies due to variability among the individual treatment devices. Hence more effort is required to ensure an adequately identical functionality among the parallel treatment channels and to verify this by testing.

In some cases it is not practical to run preparation steps on several reagent carrier bodies in parallel. An example of this is the precisely positioned deposition of drops of liquid in the production of microarrays. In this case the aim is to apply different liquids to different areas of the surface of a reagent carrier body in order to be able to simultaneously determine several different components of the sample liquid in a later assay within the same run because the different areas undergo different specific reactions with components of the sample liquid. A high throughput system with outputs of up to 5000 carriers per day is described in the publication "Kuhn et al., BIOforum Int., p. 30 ff, 2000-1".

It is also already known in the case of test strip manufacture that the carrier paper can be reeled off a storage roll and that the strip tape is passed through an immersion bath or sprayed with test substances in a continuous process. However, the coating process is followed by a very laborious process of device manufacture in which the strip tape is cut into shape and the separate paper strips are laboriously fitted into individual holders and assembled to form manageable elements.

SUMMARY OF THE INVENTION

The present invention relates to a device for preparing reagent carriers comprising a treatment device for treating reagent carrier bodies in a treatment zone, a transport device for moving the reagent carrier bodies through the treatment zone, and a control device for time-coordinated control of the treatment device and the transport device whereby the treatment device performs a predetermined treatment step on the reagent carrier bodies moving through the treatment zone.

The present invention also relates to a process for producing reagent carriers comprising a reagent for binding an analyte, the process comprising: providing reagent carrier bodies on a transport device, providing a treatment device for treating the reagent carrier bodies, transporting the carrier bodies via the transport device through a treatment zone, and treating each carrier body by applying a droplet of a reagent to the reagent carrier body via the treatment device as the reagent carrier body moves during its transport through the treatment zone.

BRIEF DESCRIPTION OF THE DRAWINGS

Embodiments of the invention are further elucidated in the following with reference to the figures.

DETAILED DESCRIPTION

Figure 1:
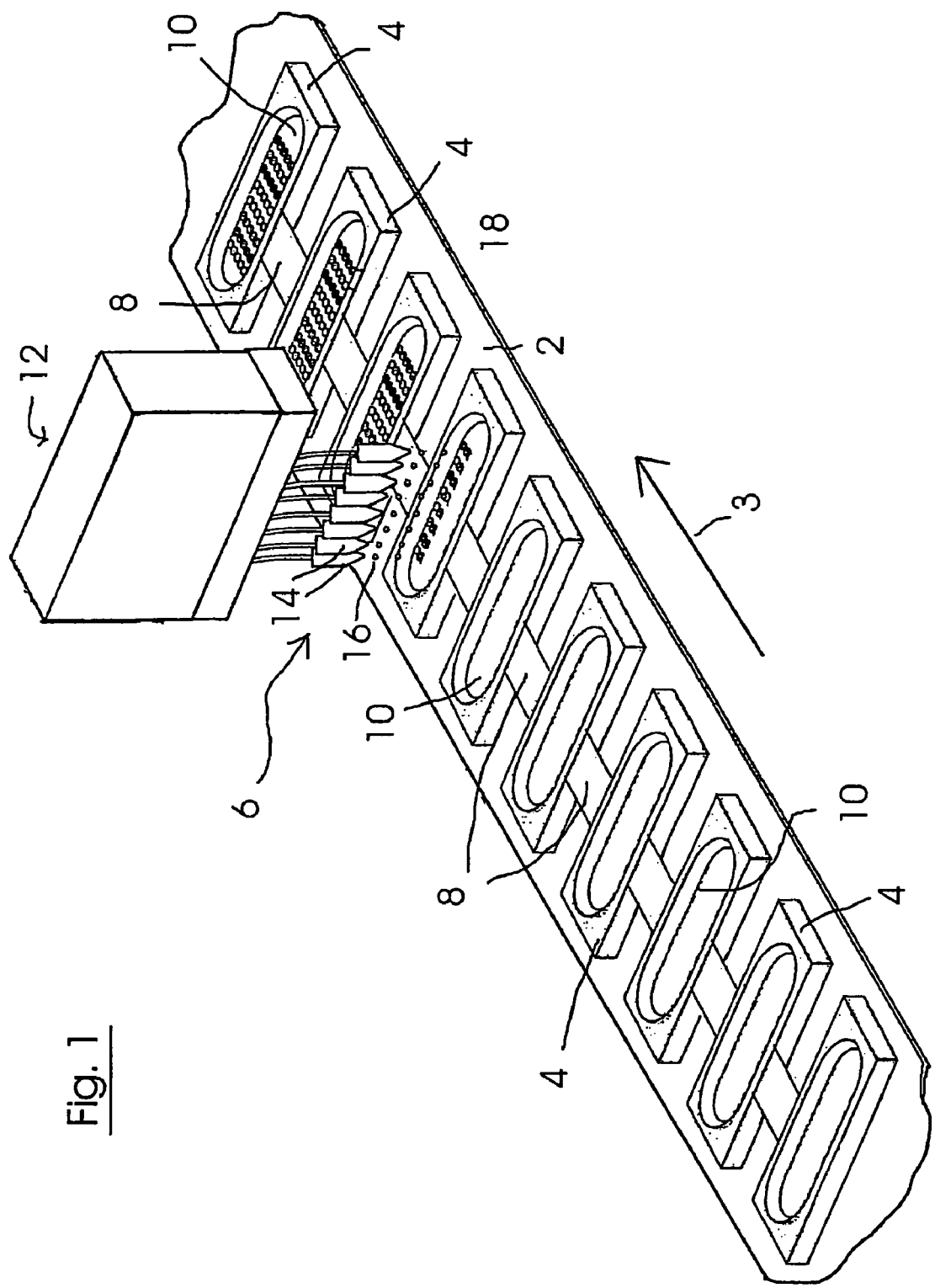
FIG. 1 shows a partial area of a preparation device according to the invention in a schematic representation in which a multiple droplet generator that is kept stationary is used as a treatment device through the treatment zone of which successive reagent carrier bodies are moved.

The object of the invention is to provide a process which by using simple means enables the production of reagent carriers having a binding capability that are suitable for determining analytes in liquids using prefabricated reagent carrier bodies at a very high output. In another aspect the object of the invention is also to provide a device for carrying out the process.

The process according to the invention for producing reagent carriers having a binding capability that are suitable for determining analytes in liquids comprises at least one step of treating a respective prefabricated reagent carrier body in particular by transferring material between a treatment device and the reagent carrier body in a preparation device and is characterized in that this at least one treatment step takes place on the moving reagent carrier body during its transport in the preparation device or during a movement of the treatment device relative to the reagent carrier body in the preparation device.

In the case of the first alternative i.e. the treatment of the reagent carrier body while it is transported in the preparation device the stationary positioning of the individual reagent carrier bodies in the treatment zone of the treatment device is omitted. Hence the reagent carrier bodies are subjected to a treatment step during their continuous passage through the relevant treatment zone. Deceleration times and acceleration times for placing the carrier body in the treatment zone and for conveying the carrier body out of the treatment zone are thus obsolete which saves an enormous amount of time in the serial preparation of the reagent carriers.

The basic idea of one aspect of the invention is to design the process sequences such that the principle realized in conventional systems of "carrying out the process in a mechanical state of rest" is omitted in as many treatment steps as possible and instead the treatment steps take place during the transport movement of the individual successive reagent carrier bodies.

Time advantages can also be achieved when using the aforementioned second process control alternative i.e. in the case that the at least one treatment step takes place during a movement of the treatment device relative to the reagent carrier body in the preparation device. Such a process control can for example comprise introducing groups of a plurality of reagent carrier bodies into a treatment zone whereupon the treatment device is then moved across the reagent carrier bodies in order to thus carry out the relevant treatment step. Afterwards the treated reagent carrier bodies can be automatically transported away and a new group of reagent carrier bodies can be provided in the treatment zone.

According to a particularly advantageous embodiment of the process according to the invention the at least one treatment step takes place on the moving reagent carrier body during its transport in the preparation device whereby the treatment device executes a synchronous movement or a movement relative to the moving reagent carrier body in the area of a treatment zone.

If several rapid treatment steps have to be performed in order to prepare the reagent carrier, then as many of these steps as possible should be carried out on the moving reagent carrier body or/and in the moving treatment device in order to carry out the fewest possible start/stop operations or stationing or/and positioning processes. However, in suitable cases it may indeed be expedient when carrying out several treatment steps to perform some of these treatment steps in a conventional manner for instance according to the aforementioned principle of running individual process steps in parallel.

The treatment steps that have to be carried out according to the inventive process on the previously provided individual reagent carrier bodies and the treatment devices that are necessary for this can be of a wide variety of types. Thus for example a first treatment step can comprise the complete overlayering of a respective reaction surface of the reagent carrier body with a substance such as a liquid by adding a metered amount of this substance to the reagent carrier body by means of a metering device.

Another treatment step can be the deposition of liquid droplets at predetermined positions on a particular surface area of the reagent carrier bodies in order to form a microarray. The liquid droplet is released by droplet generators which can for example operate according to the ink-jet principle as is known from ink-jet printers. According to the invention the reagent carrier body and the droplet generator move relative to one another and are not halted for the droplet release.

Another treatment step can be to remove substances such as liquids from the reagent carrier bodies by means of a suction device.

Another treatment step can for example be to replace solutions on reagent carrier bodies. This can for example be a rinsing step or a washing step. Also in this case the aim according to the invention is to carry out the process while essentially avoiding start/stop processes in the preparation device.

The process according to the invention can inter alia be used to produce locally defined solid phases for binding assays, the basic principle of which is disclosed for example in EP 0 939 319 A2 or EP 1 380 839 A1. Thus the process according to the invention can be used to apply a multilayered coating on a solid, non-porous reagent carrier body in which in successive treatment steps on a preferably continuously moved reagent carrier body a precoating is applied to a reagent field of the reagent carrier body, the precoated reagent carrier body is washed with an aqueous liquid and a second coating is applied to the pretreated reagent carrier body in the form of spatially defined areas on the reagent field where the second coating comprises receptor molecules that can bind to the precoating. In this case the precoating can be applied to the entire area on a part of the entire area of a reagent field of a solid reagent carrier body or also in the form of spots. The precoating is preferably applied to the entire area. The precoating is typically applied to the carrier from an aqueous solution. It can consist of any molecules that enable the binding of a second coating. The precoating preferably comprises a first partner of a high affinity binding pair such as streptavidin, avidin or biotin, as well as analogues, derivatives or conjugates of the said substances or antibodies. It is, however, also possible to apply molecules as a precoating which enable a covalent binding to the second coating such as molecules which contain an amine, a sulfite or a silyl group. After the precoated reagent carrier body has been washed, receptor molecules are then applied to the precoating in an aqueous solution in the form of small droplets. The receptor molecules can diffuse from the solution to the precoating and bind to it. Hence the process according to the invention enables the production of multianalyte carriers containing a multianalyte coating on an appropriate precoating. Carriers such as those described for example in EP 0 939 319 A2 or EP 1 380 839 A1 can be basically produced using the process of the invention.

Thus the process according to the invention can for example also be used to produce reagent carriers in which a coating solution containing receptor molecules is applied to predetermined limited areas (spots) of the reagent carrier body, the receptor molecules are bound in the spatially defined areas, the coating solution is dried and a reloading solution is applied in successive steps to the moving carrier bodies.

These process steps are elucidated for conventional process control in EP 0 939 319 A2 and in EP 1 380 839 A1, the disclosed contents of which are incorporated in the present application.

Hence the process according to the invention can be used to produce or to prepare streptavidin-coated carriers, HBc antigen carriers or multianalyte carriers. However, this still does not exhaust the potential applications.

The invention also concerns the use of a reagent carrier produced by the process according to the invention for determining analytes in a liquid.

In order to perform the method according to the invention a preparation device is proposed which is characterized by at least one treatment device for treating reagent carrier bodies, a transport device for transporting successive reagent carrier bodies through a treatment zone of the treatment device and a control device for the time-coordinated control of the treatment device and the transport device such that the treatment device in each case performs at least one predetermined treatment step on the reagent carrier bodies passing through the treatment step during the transport movement of the respective reagent carrier bodies.

Another preparation device for performing the method according to the invention is characterized by at least one treatment device for treating reagent carrier bodies, a transport device for transporting reagent carrier bodies to and from a treatment zone and a control device for controlling the treatment device and optionally the transport device, where the treatment device can be moved relative to the treatment zone under the control of the control device and can also be activated to carry out at least one predetermined treatment step during the movement in order to treat reagent carrier bodies in the treatment zone.

In the said preparation devices the treatment device preferably has a release device for the controlled metered release of at least one substance and especially a liquid onto the reagent carrier bodies. According to a further development of the preparation device according to the invention the release device can comprise means for the position-selective deposition of liquid droplets on the reagent carrier bodies.

In addition or alternatively the treatment device can have a removal device for removing at least one substance and in particular a liquid from the reagent carrier bodies. By combining a release device and a removing device, it is possible to simultaneously exchange liquids on the reagent carrier body.

The treatment device preferably also comprises a rinsing device for reagent carrier bodies. Furthermore, the treatment device can comprise a drying device.

In addition or alternatively the treatment device can comprise irradiation means or optical monitoring means for reagent carrier bodies in the preparation device.

FIG. 1 shows a perspective view of a section of a conveyor belt 2 which is part of a transport device for reagent carrier bodies 4. The reagent carrier bodies 4 are prefabricated reaction vessels and can for example be injection-moulded parts made of polystyrene or such like. In the case shown as an example in FIG. 1 the individual reagent carrier bodies 4 are transported in a group through the treatment zone 6 by means of the transport device 2, the reagent carrier bodies 4 being for example connected together by connecting strips 8 that can be easily removed at a later time. In other embodiments of the invention the prefabricated reagent carrier bodies 4 can be transported on the conveying device 2 without connecting strips and thus separate from one another.

The upper side of the reagent carrier bodies 4 are hollowed out in a trough shaped manner where the bottom of the trough has the surface 10 of the reagent carrier body 4 that is to be treated. The outer dimensions of a reagent carrier body 4 are ca. 22 mm×7 mm×3 mm in a particular example. Of course other dimensions and designs of the reagent carriers are possible.

A droplet generator 12 that operates according to the inkjet principle and is controlled by an electronic control unit (not shown) is shown schematically in FIG. 1 as the treatment device. The droplet generator 12 is used to deposit liquid droplets at predetermined positions on the area 10 of the reagent carrier bodies 4. In the example of FIG. 1 the droplet generator 12 comprises eight droplet discharge jets 14 which are supplied with certain liquids from liquid reservoirs which are then discharged as drops onto the reagent carrier bodies 4. The droplets 16 reach the surface 10 of the respective reagent carrier body that is passing through the treatment zone 6 in free flight over a distance of several millimetres. It is preferable but not absolutely essential that the reagent carrier bodies 4 are continuously transported at a constant speed and drops are generated by the droplet generator 12 at a constant frequency.

Monitoring means of the control device ensure that the droplet discharge by the droplet generator 12 and the transport of the reagent carrier bodies 4 are coordinated in such a manner that droplets 16 can only reach the surface areas 10 of the reagent carrier bodies 4 in the predetermined manner. The arrangement of FIG. 1 can be used to readily produce several identical areas (replicates) at a high cycle rate. In the case of the reagent carrier bodies 4 that have already been treated in FIG. 1, replicates are shown in the same shade of grey and different reactants are labelled with a different shades of grey. The reagent carrier bodies 4 are prepared in this manner with areas of different reactivity in the assay.

The arrangement of FIG. 1 if required allows a process control in which the relative movement between the reagent carrier bodies 4 and droplet generator 12 occurs at a constant speed and the individual droplet generators (jets 14) are operated at a constant time frequency, but at a frequency that is individually slightly different from jet 14 to jet 14. This results in patterns with individual distances between the respective replicates which can be used to identify the droplet type or the analyte type in the assay.

In test runs reagent carrier bodies 4 were conveyed through the treatment zone 6 at a rate of advance of about 10 cm/s. The droplet generators 14 were operated at a frequency of 500 Hz to prepare reagent carrier samples having ca. 25 replicates per liquid type. The achieved capacity was more than 50,000 samples per hour. The output performance can be considerably increased by optimization measures.

Figure 2:
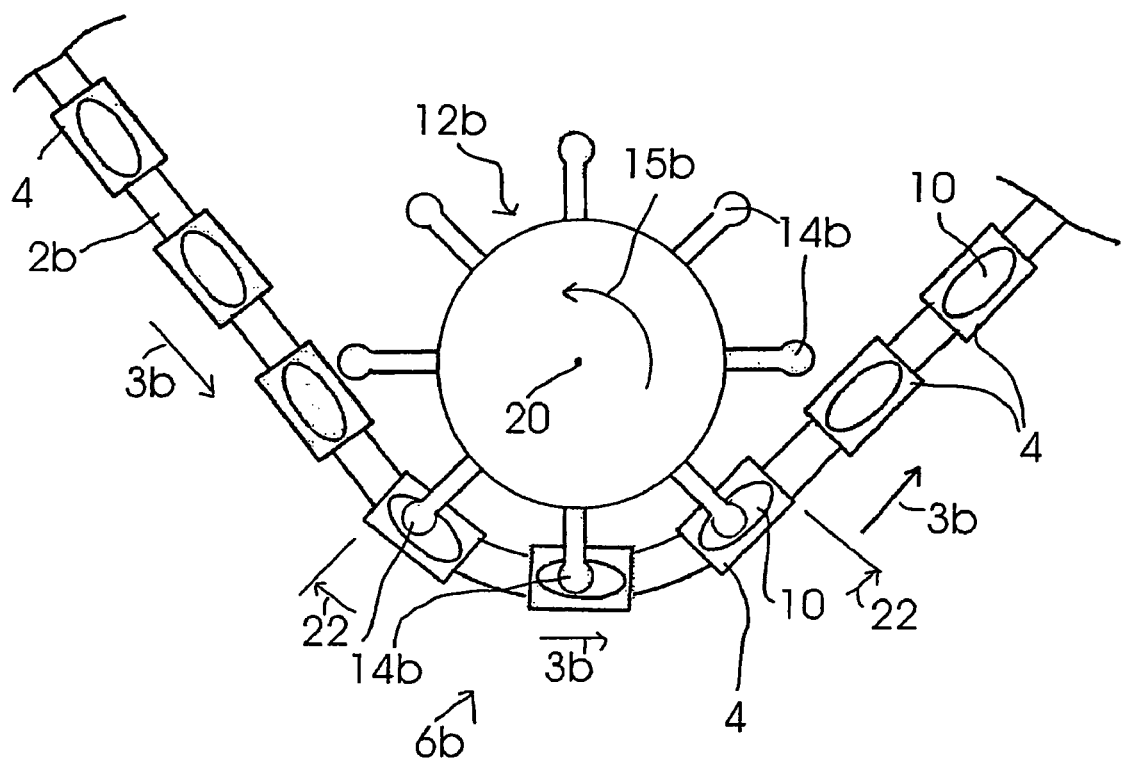
FIG. 2 shows a preparation device according to the invention in a schematic representation in which the reagent carrier bodies as well as the treatment device are in motion in a treatment zone area.

FIG. 2 shows another embodiment of an aspect of the invention in a schematic top-view and this aspect concerns the continuous movement of the reagent carrier bodies 4 as well as the treatment device 12b during the treatment of the reagent carrier bodies 4.

The transport device transports the reagent carrier bodies 4 one after the other along the path 3b. During this the reagent carrier bodies 4 pass through a treatment zone 6b in which they are treated by the treatment device 12b. In this example the treatment device 12b comprises eight treatment heads 14b which project radially outwards from a common centre 20 and are separated from one another by the same angular distances and which rotate around the common centre 20. The direction of rotation of the treatment device 12b indicated by the arrow 15b and its rotational speed are matched under the control of an electronic control device (not shown) to the movement of the reagent carrier bodies 4 in such a manner that the reagent carrier bodies 4 passing through the treatment zone 6b are accompanied by an individually allocated treatment head 14b over a predetermined angular range 22 and are thus treated. In the example of FIG. 2 three reagent carrier bodies 4 are in each case simultaneously treated during the common movements of the reagent carrier bodies 4 and the treatment device 12. The treatment device 12b in the embodiment example of FIG. 2 can for example be a liquid dispensing device which can dispense liquid in a metered manner onto the reagent carrier body 4 by each of the treatment heads 14b. In the case of very high throughput rates it may be appropriate to select the release time in such a manner that liquid is already ejected before the respective reagent carrier body 4 is positioned below the outlet jet.

Monitoring means of the control device are preferably used to synchronize the triggering of the liquid transfer with the movement of the reagent carrier. Such monitoring means can for example be light barriers, image recording devices such as CCD sensors etc.

Furthermore, it may be advantageous to cascade the process of supplying liquid to the reagent carrier body such that liquid is applied to the reagent carrier body not in a single dose but rather in several doses from N channels which are supplied by a common storage vessel.

In the case of the principle outlined in FIG. 2 the treatment heads 14b may move at a speed that is different to that of the reagent carrier bodies 4 as they pass through the treatment zone 6b such that each reagent carrier body 4 can be acted upon by several treatment heads 14b in succession in order for example to carry out a suction step, a liquid supply step and optionally an irradiation step in succession.

The functions and constructional systems of suitable liquid dispensing devices, suction devices, rinsing and washing devices and detection devices are known to a person skilled in the art so that it may be left to his discretion to use one or more such devices in the manner according to the invention in a preparation device of the type that is here under consideration and to carry out the process according to the invention in order to avoid as largely as possible start and stop processes in the handling of the reagent carrier bodies 4 when producing or preparing reagent carriers capable of binding.

It should be pointed out that the reagent carrier bodies 4 shown in the figures only represent examples. The invention can of course also be carried out using reagent carrier bodies of other shapes.

What is claimed is:

1. A process for producing reagent carriers comprising a reagent for binding an analyte, the process comprising:
    providing reagent carrier bodies on a continually moving transport device,
    providing a treatment device for treating the reagent carrier bodies, wherein the treatment device comprises one or more of a drying device, an irradiating device, an optical monitoring device, a removal device, and a release device,
    transporting the carrier bodies via the transport device through a treatment zone wherein the treatment device remains positioned over the transport device through the treatment zone and wherein the treatment device and reagent carrier bodies move at a constant speed relative to one another through the treatment zone, and
    treating each carrier body via the treatment device as the reagent carrier body moves during its transport through the treatment zone.

2. The process of claim 1 wherein the treatment step occurs as the treatment device moves relative to the treatment zone.

3. The process of claim 1 wherein the treatment device comprises at least one droplet generator comprising droplet discharge jets comprising a liquid provided from a liquid reservoir.

4. The process of claim 3 wherein the treatment step further comprises removing a liquid from the reagent carrier bodies.

5. The process of claim 1 wherein the reagent is streptavidin or HBc antigen.

6. The process of claim 3 wherein the at least one droplet generator operates at a constant time frequency.

7. The process of claim 3 wherein the release device comprises more than one droplet generator and each droplet generator operates at a different constant time frequency.

* * * * *

UNITED STATES PATENT AND TRADEMARK OFFICE
CERTIFICATE OF CORRECTION

PATENT NO. : 7,608,466 B2 Page 1 of 1
APPLICATION NO. : 11/156855
DATED : October 27, 2009
INVENTOR(S) : Hans Hornauer It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 452 days.

Signed and Sealed this

Twelfth Day of October, 2010

David J. Kappos
*Director of the United States Patent and Trademark Office*